United States Patent
Wu et al.

(10) Patent No.: US 7,474,396 B2
(45) Date of Patent: Jan. 6, 2009

(54) RAMAN SPECTROSCOPY SYSTEM AND METHOD USING A SUBWAVELENGTH RESONANT GRATING FILTER

(75) Inventors: Wei Wu, Mountain View, CA (US); Zhiyong Li, Redwood city, CA (US); Shih-Yuan Wang, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 369 days.

(21) Appl. No.: 11/257,073

(22) Filed: Jan. 17, 2006

(65) Prior Publication Data
US 2007/0165214 A1 Jul. 19, 2007

(51) Int. Cl.
*G01J 3/44* (2006.01)
*G01J 3/00* (2006.01)

(52) U.S. Cl. ...................... 356/301; 356/300
(58) Field of Classification Search ................. 356/301, 356/300–334
See application file for complete search history.

(56) References Cited

U.S. PATENT DOCUMENTS

| | | | |
|---|---|---|---|
| 5,247,343 A | | 9/1993 | Burch |
| 5,598,300 A | * | 1/1997 | Magnusson et al. ......... 359/566 |
| 5,726,805 A | * | 3/1998 | Kaushik et al. ............. 359/589 |
| 5,772,905 A | | 6/1998 | Chou |
| 5,910,940 A | * | 6/1999 | Guerra .................... 369/275.1 |
| 6,035,089 A | * | 3/2000 | Grann et al. ................ 385/129 |
| 6,285,020 B1 | * | 9/2001 | Kim et al. .................. 250/216 |
| 6,309,580 B1 | * | 10/2001 | Chou ........................ 264/338 |
| 6,362,919 B1 | * | 3/2002 | Flanders .................... 359/497 |
| 6,552,842 B2 | * | 4/2003 | Simpson et al. ............. 359/318 |
| 6,597,721 B1 | * | 7/2003 | Hutchinson et al. ........... 372/98 |
| 6,661,952 B2 | * | 12/2003 | Simpson et al. .............. 385/37 |
| 6,972,906 B2 | * | 12/2005 | Hasman et al. ............. 359/569 |
| 7,094,595 B2 | * | 8/2006 | Cunningham et al. ..... 435/287.2 |
| 7,164,514 B2 | * | 1/2007 | Raguin .......................... 359/3 |
| 7,237,940 B2 | * | 7/2007 | Yu et al. ..................... 362/621 |
| 7,282,748 B2 | * | 10/2007 | Takeda et al. ................. 257/98 |
| 2002/0148963 A1 | | 10/2002 | Claiborne et al. |
| 2003/0039446 A1 | * | 2/2003 | Hutchinson et al. ........... 385/39 |

(Continued)

FOREIGN PATENT DOCUMENTS

WO    WO98/57200    12/1998

OTHER PUBLICATIONS

Allan S.P. Chang et al., "A New Two-Dimensional Subwavelength Resonant Grating Filter Fabricated By Nanoimprint Lithography", 2001 Annual Meeting of the IEEE Lasers & Electro-Optics Society, Nov. 12-15, 2001, San Diego, CA., 3 pages.

*Primary Examiner*—L. G. Lauchman
*Assistant Examiner*—Jarreas C Underwood

(57) ABSTRACT

A Raman spectroscopy system is disclosed which includes a sub-wavelength resonant grating filter and a photodiode with integrated sub-wavelength resonant grating filter are disclosed. The resonant grating filter comprises an array of diffraction elements having a periodic spacing that is less than the wavelength of radiation to be filtered and which are formed over a waveguide layer. The filter, which can reject a specific wavelength of radiation, can be placed between a Raman sample and a Raman detector in order to filter radiation that is elastically scattered from the sample while transmitting other wavelengths. The wavelength rejected by the filter can be selected by tilting the filter with respect to the radiation incident upon the filter.

39 Claims, 7 Drawing Sheets

U.S. PATENT DOCUMENTS

2004/0071180 A1    4/2004  Wang
2004/0120644 A1*   6/2004  Chou et al. .................. 385/37
2004/0181344 A1*   9/2004  Stephanopoulos et al. .... 702/20
2004/0184732 A1    9/2004  Zhou
2004/0239869 A1   12/2004  Cavanaugh et al.
2005/0195485 A1*   9/2005  Hirai et al. .................. 359/569

* cited by examiner

RAMAN SPECTROSCOPY SYSTEM AND METHOD USING A SUBWAVELENGTH RESONANT GRATING FILTER

BACKGROUND

In Raman spectroscopy, a sample comprised of one or more molecules can scatter or absorb a photon incident upon the sample. The molecule-photon interaction can temporarily change the energy state of a molecule within the sample, i.e., the energy state of a molecule can be changed from an initial state to an excited state through a dipole-allowed transition. After a short period of time, typically less than about $10^{-14}$ seconds, the molecule can relax from its excited state with the concomitant emission of a new photon. The energy of emitted photons as well as photons scattered by the sample can be classified into one of three categories.

First, an emitted photon having less energy (i.e., lower frequency) than the incident photon is referred to as a "Stokes" emission. Stokes emissions occur when a molecule absorbs incident photon energy and relaxes into an excited rotational and/or vibrational state. Each molecular species in a sample can generate a characteristic set of Stokes emissions, the intensity of which is proportional to the density in the sample of the molecular species.

Second, an emitted photon having more energy (i.e., higher frequency) than the incident photon is called an "Anti-Stokes" emission. Anti-Stokes emissions can occur when an incident photon interacts with a molecule already in an excited state. During the molecule-photon interaction, the molecule can decay from the excited state to a lower energy state. The anti-Stokes photon will be emitted with the energy of the incident photon plus the difference in energy between the molecule's excited state and its lower energy state. As with Stokes emissions, each molecular species in a sample can generate a characteristic set of anti-Stokes emissions, the intensity of which is proportional to the density in the sample of the molecular species. Stokes and Anti-Stokes emissions (collectively Raman emissions) can provide quantitative information about the molecular species contributing to the scattering process.

Third, an elastically scattered photon has the same energy as the incident photon. Sample molecules that contribute to elastic scattering return to their initial energy state. Typically, the intensity of elastic (or Rayleigh) scattered photons dominates the scattering/emission spectra. different filter arrangements have been used to remove or reduce the intensity of the Rayleigh scattered photons. For example, triple monochromators, edge filters, and notch filters have been used. These filters arrangements are expensive and/or result in the attenuation of at least a portion of the Raman spectrum.

SUMMARY

A Raman system comprises (i) a radiation source; (ii) a detector positioned to receive radiation from the radiation source; and (iii) a sub-wavelength resonant grating filter positioned between the radiation source and the detector, wherein the sub-wavelength resonant grating filter comprises a waveguide layer and a patterned layer comprising an array of diffraction elements.

An exemplary Raman system comprises (i) means for irradiating a sample with excitation radiation of a single wavelength; (ii) means for detecting scattered radiation from the sample irradiated with the excitation radiation; and (iii) a sub-wavelength resonant grating filter for removing from the scattered radiation a characteristic wavelength of radiation prior to detecting the scattered radiation, wherein the sub-wavelength resonant grating filter comprises a waveguide layer and a patterned layer comprising an array of diffraction elements.

A method is disclosed for measuring by Raman spectroscopy one or more selected constituents of a chemical composition, comprising (i) irradiating with a substantially monochromatic radiation source a chemical composition comprising the one or more chemical constituents; (ii) directing radiation scattered and/or emitted from the chemical composition through a sub-wavelength resonant grating filter, the sub-wavelength resonant grating filter comprising a waveguide layer and an array of diffraction elements having a characteristic period and a characteristic height, and (iii) detecting radiation transmitted through the filter.

An integrated photodiode-filter comprises a substrate, at least one photodiode comprising an active surface formed in and on the substrate; and an integrated sub-wavelength resonant grating filter, wherein the sub-wavelength resonant grating filter comprises a waveguide layer formed on the active surface and a patterned layer comprising an array of diffraction elements formed on the waveguide layer.

BRIEF DESCRIPTION OF THE DRAWINGS

The following detailed description of preferred embodiments can be read in connection with the accompanying drawings in which like numerals designate like elements and in which.

DETAILED DESCRIPTION

Figure 1:
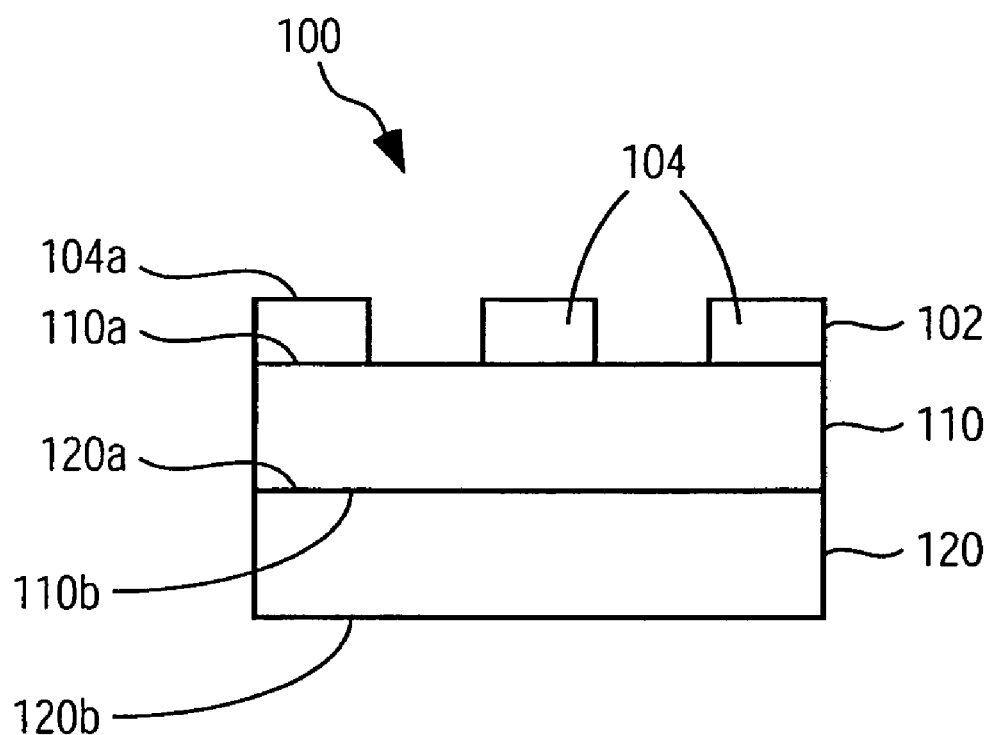
FIG. 1 shows a cross-sectional schematic of an exemplary sub-wavelength resonant grating filter.

A Raman spectroscopy system is disclosed comprising a sub-wavelength resonant grating filter, which can be configured of one or more filters. The filters can be produced from the same or different wafers (e.g., glass or other suitable materials). The sub-wavelength resonant grating filter, which can be placed between a sample and a detector, can be used to reject a specific wavelength of radiation incident upon the filter and transmit other wavelengths in order to reduce the intensity of elastically scattered radiation incident upon the detector. Thus, the sub-wavelength resonant grating filter can substantially reduce the intensity of elastically scattered photons emitted from the sample while the Raman scattered radiation can pass substantially un-attenuated through the filter to be recorded by a suitable spectrometer.

An exemplary sub-wavelength resonant grating filter has an extinction ratio of greater than about 10 (e.g., the ratio of the intensity of a characteristic wavelength of radiation to other wavelengths of radiation incident upon the filter is reduced by the filter by at least 10, more preferably by at least 100, most preferably by at least 1000). An alternate sub-wavelength resonant grating filter can reduce the intensity of elastically scattered radiation by at least 90% (e.g., by at least 90, 92, 94, 96, 98, 99 or 99.9%).

An exemplary sub-wavelength resonant grating filter, which can provide discrete wavelength discrimination, comprises a single patterned layer that is optically coupled to a waveguide layer. The patterned layer (i.e., grating layer) can overlie the waveguide layer and comprise a repeating array of diffraction elements. The waveguide layer can be a substantially planar layer. Both the patterned layer and the waveguide layer can be formed from a high refractive index, non-absorbing material. The filter can comprise an optional substrate layer. The substrate layer, if provided, can support the waveguide layer.

The patterned layer can comprise a linear (i.e., one-dimensional) array or, alternatively, a two-dimensional array of diffraction elements. The array of diffraction elements can form a two-dimensional grating structure that is periodic is two orthogonal directions (x, y). The diffraction elements can be cylindrical pillars, but alternative shapes such as rectangular pillars, cones or any other suitable shape can be provided. Diffraction elements can be formed over the waveguide layer. In the alternative, the diffraction elements can be recessed within the patterned layer (i.e., the diffraction elements can comprise an array of circular holes).

The diffraction elements can have at least one lateral dimension (e.g., diameter, length or width) of less than about 500 nm (e.g., less than about 350 nm), and a height above the waveguide layer (or depth into the patterned layer) of less than about 500 nm (e.g., less than about 350 nm). The shape of the diffraction elements can be represented by an aspect ratio, which, as defined herein, is the ratio of the height of the element to a lateral dimension of the element. An exemplary resonant grating filter comprises a two-dimensional array of diffraction elements having an aspect ratio of between about 0.1 and 2, more preferably between about 0.2 and 1.

In embodiments where the grating comprises a one-dimensional array of elements, the array has a period $D_x$ in the x-direction that is less than the wavelength of the radiation to be filtered. In embodiments where the grating comprises a two-dimensional array of elements, the array has a period $D_x$ in the x-direction and a period $D_y$ in the y direction. Both $D_x$ and $D_y$ are less than the wavelength of the radiation to be filtered. The sub-wavelength periods $D_x$ and $D_y$ can be, but not necessarily, equal.

The period of the diffraction elements, which is selected to be less than the wavelength of the radiation to be processed, can be less than about 1.2 micron (e.g., about 0.2, 0.4, 0.6, 0.8 or 1.0 micron±0.1 micron). The period is a measure of the distance from a point on one diffraction element to a corresponding point on a neighboring diffraction element. Thus, the period of the diffraction elements is the sum of a distance between two elements, d, and a lateral dimension of an element, l, along a periodic direction. As used herein, the duty cycle is the ratio of a lateral dimension of an element divided by the period along a periodic direction within the array. An exemplary resonant grating filter has a duty cycle of about 50% (i.e., l≅d), but the duty cycle can be less than or greater than 50%.

The grating layer, the waveguide layer and the optional substrate layer comprise optically transparent dielectric materials. The grating layer has an effective index of refraction, $n_{eff}$. The waveguide layer and the optional substrate layer have indices of refraction $n_w$ and $n_s$, respectively. The index of refraction of the waveguide layer can be greater than the effective index of refraction of the grating layer, and greater than the index of refraction of the substrate layer, if provided. "Optical wavelength" is defined as the wavelength of an electromagnetic wave in a given medium, and is equal to the wavelength of the wave in vacuum divided by the refractive index of the medium.

The grating layer and the waveguide layer can be formed from materials such as silicon nitride, silicon oxide, silicon oxynitride, hafnium oxide, tantalum oxide, and the like. The grating layer and/or the waveguide layer can be doped.

The thickness of the waveguide layer can be less than about 500 nm (e.g., about 100, 200, 300 or 400 nm≅50 nm). The optional substrate layer can comprise a ceramic material having a thickness of greater than about 0.5 mm. Exemplary substrate materials include silicon oxide (e.g., quartz, fused silica), aluminum oxide and the like. An exemplary sub-wavelength resonant grating filter comprises a fused silica substrate having a thickness of about 1 mm.

Because the resonant grating filter comprises only a single patterned layer that is formed over a waveguide layer, the resonant grating filter can be formed on a variety of substrate materials and incorporated into a Raman system. For example, the substrate can comprise a lens such as an optical lens used to focus or direct radiation scattered from the sample. The substrate can comprise a photodiode or a photodiode array that is incorporated into the Raman detector. In an exemplary embodiment, a sub-wavelength resonant grating filter can be formed over the active surface area of one or more photodiodes. The resonant grating filter can be formed over multi-element photodiode arrays, CCD-type arrays, active pixel sensor arrays, and the like.

In operation, photons scattered from a Raman sample are directed onto the grating surface of the sub-wavelength resonant grating filter, typically at normal incidence to the plane of the grating layer. At a resonant wavelength $\lambda_{res}$ incident upon the filter, diffraction from the grating elements produces evanescent waves in the plane of the waveguide. Resonance can occur when a surface-propagating wave is trapped within the grating/waveguide region. If the trapped wave is coupled into a mode of the waveguide, the radiation will resonate and result in a total reflection of the incident beam in a narrow bandwidth. If the incident radiation is not within the resonant bandwidth, most of the energy of the incident beam will propagate (i.e., be transmitted) through the filter.

Reflection over a narrow bandwidth can occur if, in addition to the period of the grating being less than the wavelength of the incident beam, the effective refractive index of the grating, $n_{eff}$, is greater than the refractive index of the medium above the grating (i.e., air) and, as mentioned above, the index of refraction of the waveguide layer is greater than both the effective refractive index of the grating layer and the refractive index of the substrate layer, if provided.

The value of the resonant wavelength, which is primarily a function of the grating period, can be expressed as $\lambda_{res}=aD+b$, where D is the grating period and a and b are constants. For a beam of radiation directed at normal incidence to the plane of the grating $\lambda_{res}=\lambda^{\circ}_{res}$, where $\lambda^{\circ}_{res}$ is the resonant wavelength for radiation directed at normal incidence. The resonant reflective response of the filter can be modulated (i.e., tuned) by varying the angle of incidence of the incoming beam with respect to the plane of the filter surface.

The bandwidth and extinction ratio of the filter are primarily a function of the thickness of the grating layer. For example, decreasing the thickness (i.e., height) of the grating structures will decrease the full-width-at-half-maximum (FWHM) of the spectral response. On the other hand, decreasing the thickness of the grating structures will decrease the extinction ratio.

While the diffraction elements can have a height that is greater than the thickness of the waveguide layer, a preferred resonant grating filter comprises an array of diffraction elements having a height that is less than the thickness of the waveguide layer. For example, the thickness of the waveguide layer can be 1.5, 2 or 2.5 times greater than the thickness (i.e., height) of the diffraction elements. An exemplary Raman system comprises a resonant grating filter having an array of diffraction elements configured to maximize the extinction ratio for the excitation wavelength supplied by the radiation source.

The grating layer and waveguide layer can be formed using available thin film deposition techniques such as magnetron sputter vacuum deposition (MSVD), chemical vapor deposition (CVD), spray pyrolysis (i.e., pyrolytic deposition), atmospheric pressure CVD (APCVD), low-pressure CVD (LPCVD), plasma-enhanced CVD (PECVD), plasma assisted CVD (PACVD), thermal or electron-beam evaporation, cathodic arc deposition, plasma spray deposition, or wet chemical deposition (e.g., sol-gel, etc.). Available lithography (i.e., pattern and etch processes) can be used to form the diffraction elements. An exemplary method of making a sub-wavelength resonant grating filter uses nanoimprint lithography (NIL). Nanoimprint lithography can be used to form the diffraction elements in the grating layer. The formation of patterned thin films on a substrate using nanoimprint lithography is disclosed in U.S. Pat. Nos. 6,309,580 and 5,772,905 and in U.S. Patent Application Publication No. 2004/0120644, the entire contents of which is disclosed herein by reference.

FIG. 1 illustrates a cross-sectional schematic view of a sub-wavelength resonant grating filter. The sub-wavelength resonant grating filter 100 comprises a patterned layer 102, a waveguide layer 110, and an optional substrate layer 120. The single patterned layer 102 comprises an array of diffraction elements 104 each having an upper surface 102a. Waveguide layer 110 and substrate layer 120 comprise upper surfaces 110a and 120a, respectively, and lower surfaces 110b and 120b respectively. The grating layer 102 and the waveguide layer 110 can comprise the same material or different materials.

The sub-wavelength resonant grating filter can comprise an anti-reflective coating layer (not shown). An anti-reflective coating can be formed on at least one surface 102a, 110a, 110b, 120a or 120b.

Figure 2:
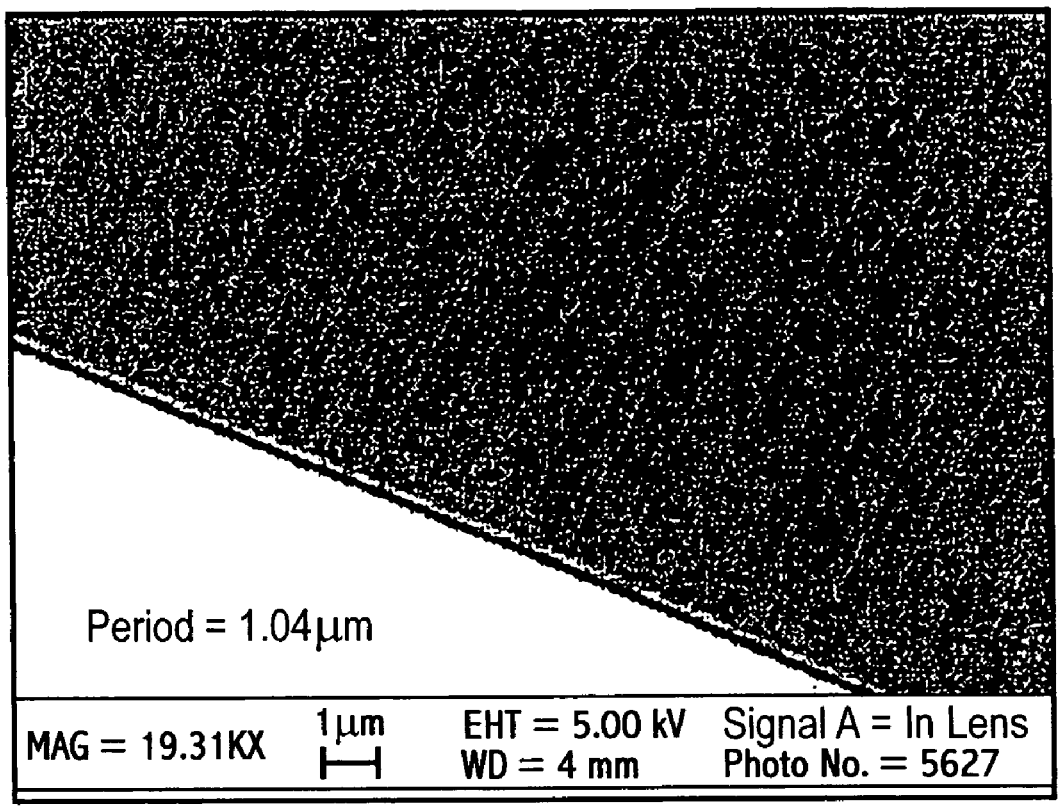
FIG. 2 shows a scanning electron microscopy (SEM) image of an exemplary one-dimensional sub-wavelength resonant grating filter made by nanoimprint lithography.

FIG. 2 shows a scanning electron micrograph of an exemplary one-dimensional resonant grating filter designed to operate at 1.5 micron spectral range. The filter comprises an array of linear silicon nitride diffraction elements formed over a silicon nitride waveguide layer. The silicon nitride was deposited on a fused silica substrate using plasma-enhanced chemical vapor deposition (PECVD) and the grating structure was fabricated using nanoimprint lithography.

The total thickness of the silicon nitride (grating layer plus waveguide layer) is about 350 nm. The height of the grating structures is about 50 nm. The period of the grating is about 1.04 micron and the width of the diffraction elements is about 500 nm (i.e., the duty cycle of the resonant grating filter is about 1). The refractive index of the silicon nitride is about 1.9 and the refractive index of the fused silica substrate is 1.46. The spectral response of the one-dimensional filter is shown in FIG. 3.

Figure 3:
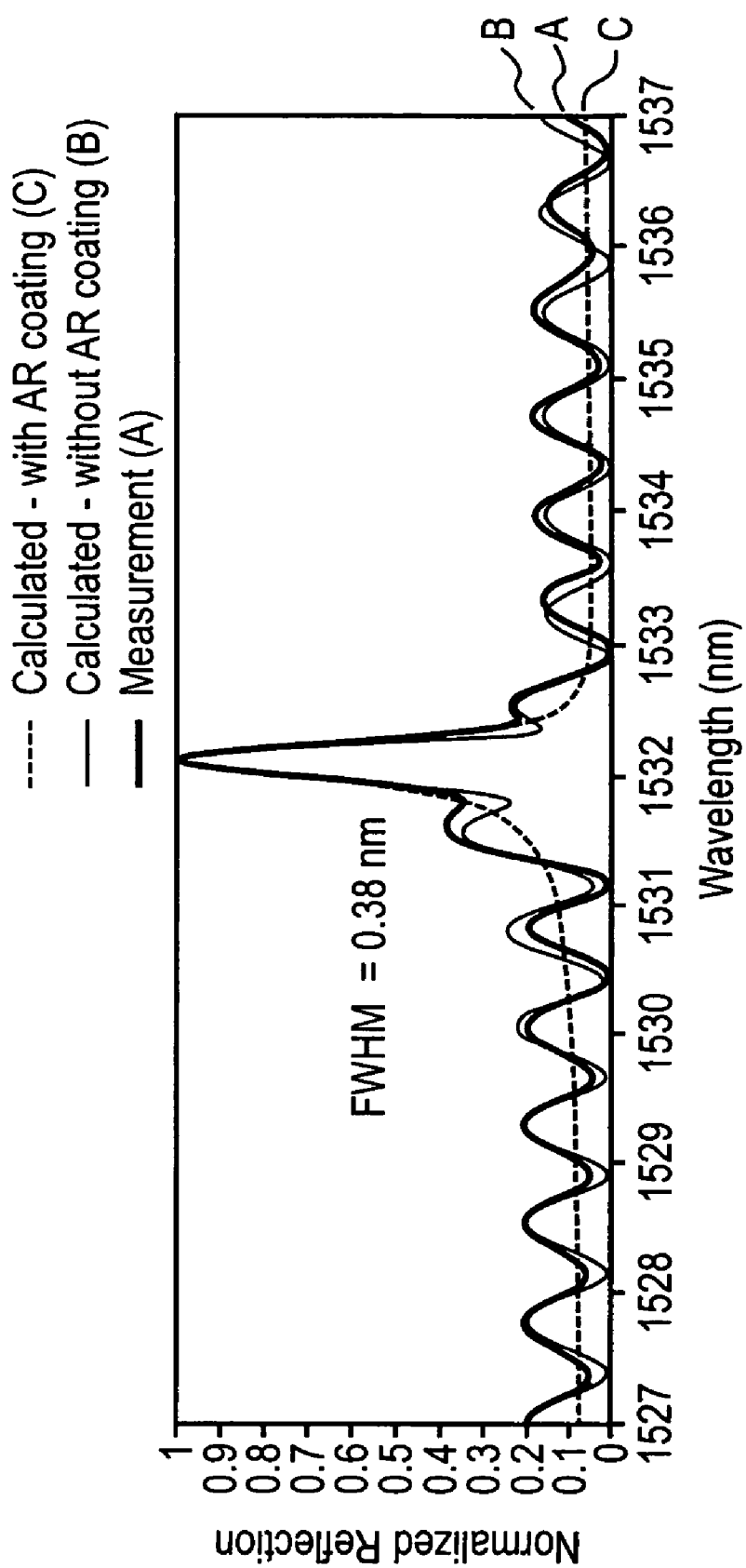
FIG. 3 shows the spectral reflectance for an exemplary one-dimensional sub-wavelength resonant grating filter.

FIG. 3 shows a plot of spectral reflectance versus wavelength for transverse electric (TE)-polarized radiation at normal incidence upon the exemplary filter shown in FIG. 2 (Curve A). At a resonant wavelength, $\lambda°_{res}$, of about 1532 nm, about 98% peak reflectance and a full width at half maximum (FWHM) of about 0.38 nm were recorded. The data (Curve A) are in agreement with the theoretical response (Curve B) that was calculated based on Rigorous Coupled-Wave Analysis (RCWA) using the fabrication parameters for the filter shown in FIG. 2. The oscillations in the sidebands are due to Fresnel reflections at the upper and lower surfaces of the fused silica substrate. As shown by Curve C, which is a further FCWA calculation, coating at least one side of the substrate with an anti-reflection coating can eliminate the Fresnel reflections.

Figure 4:
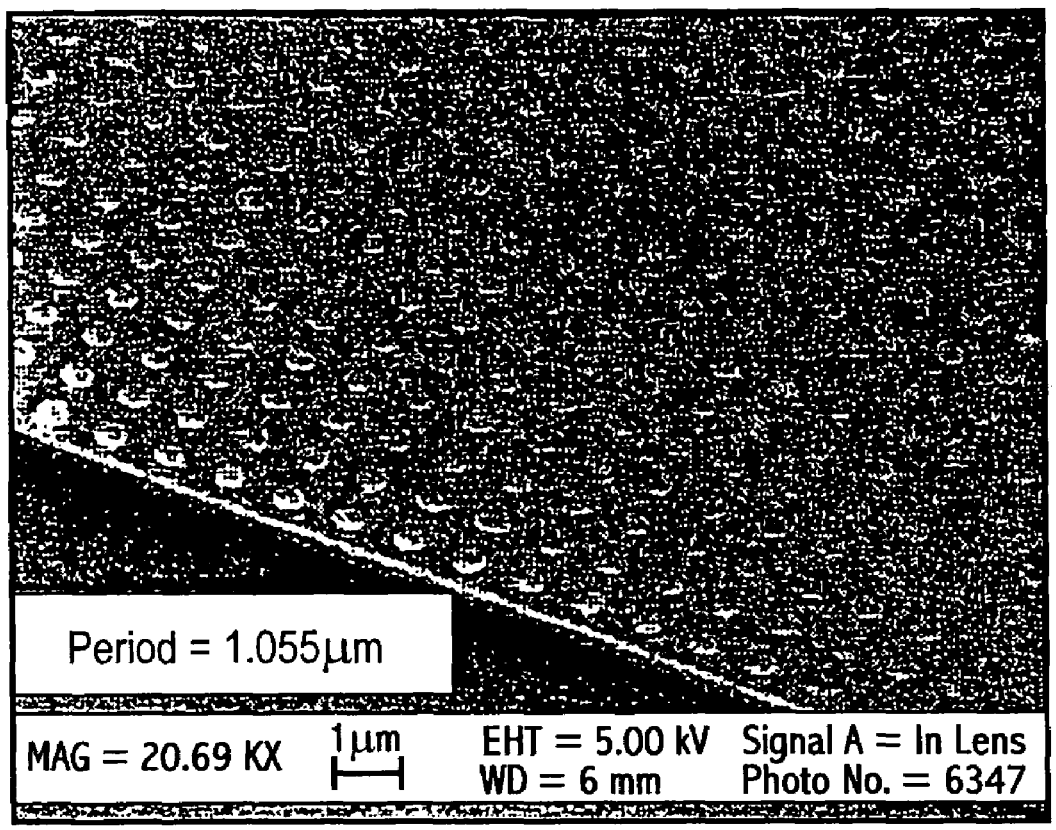
FIG. 4 shows a scanning electron microscopy (SEM) image of an exemplary two-dimensional sub-wavelength resonant grating filter made by nanoimprint lithography.

FIG. 4 shows a scanning electron micrograph of a two-dimensional resonant grating filter designed to operate at 1.5 micron spectral range. The filter comprises a silicon nitride pillar array formed over a silicon nitride waveguide layer. The period of the pillar array is about 1.055 micron along both the x- and y-direction. Each pillar has a diameter of about 500 nm and a height above the waveguide layer of about 50 nm. The thickness of the waveguide layer is about 350 nm.

Figure 5:
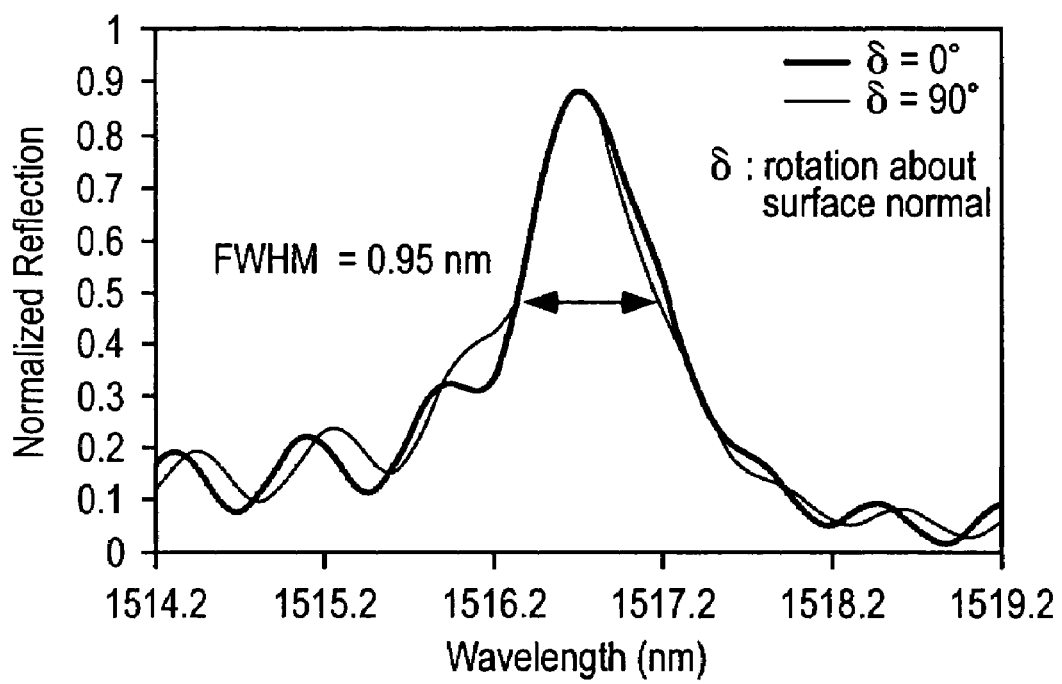
FIG. 5 shows the spectral reflectance for an exemplary two-dimensional sub-wavelength resonant grating filter.

The spectral response for two orthogonal polarizations (achieved by performing a measurement before and after rotating the filter by 90° along its surface normal) is shown in FIG. 5. At a resonant wavelength $\lambda°_{res}$, of about 1517 nm, a peak reflectance of about 88% and a full width at half maximum (FWHM) of about 0.95 nm were recorded. Because the pillar array has the same period and duty cycle along two perpendicular directions, the spectral response of the filter is substantially independent of polarization at normal incidence.

Figure 6:
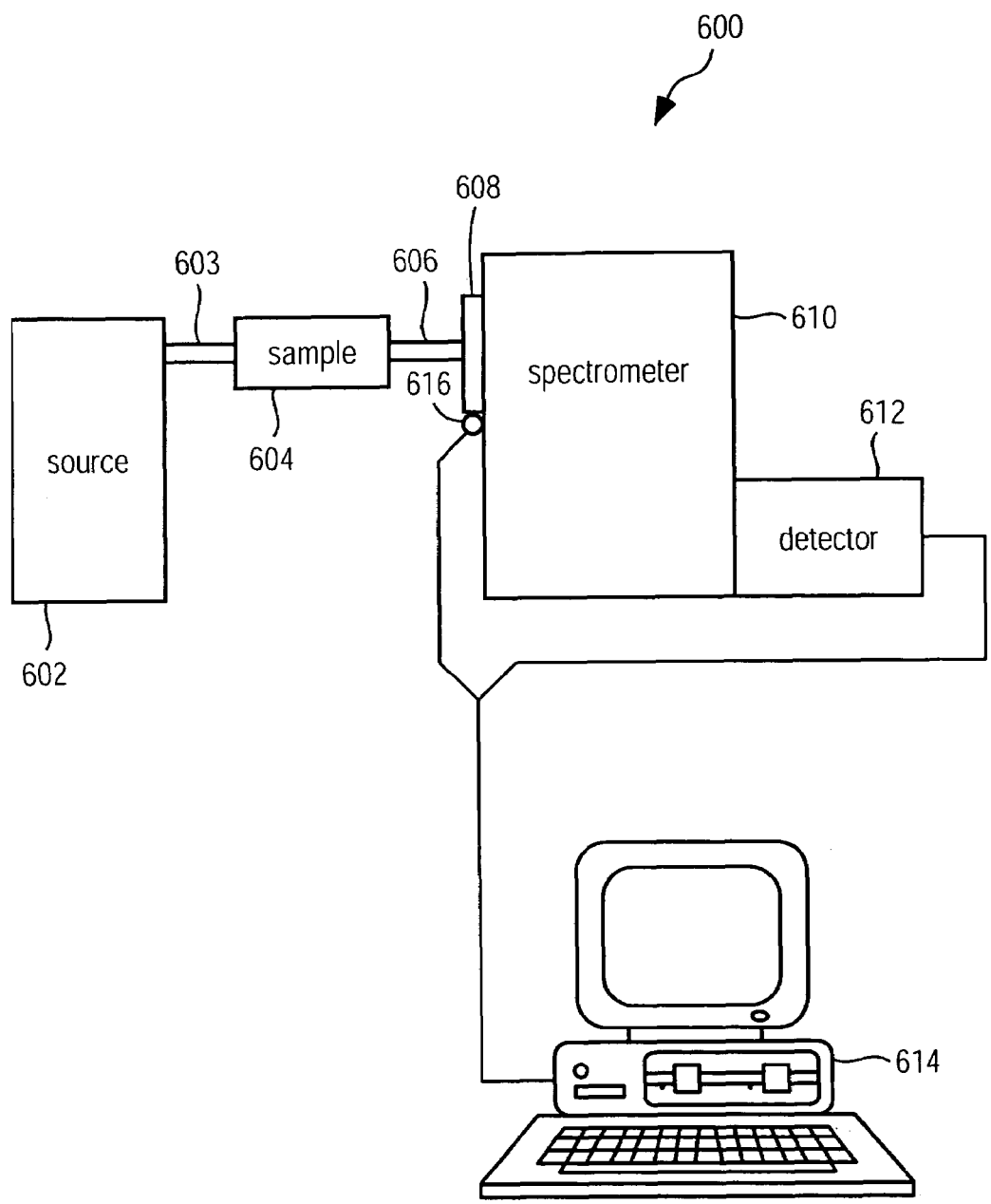
FIG. 6 is a schematic illustration of a Raman system comprising an exemplary sub-wavelength resonant grating filter.

An exemplary Raman system 600, which is shown schematically in FIG. 6, can comprise a radiation source 602; a means, such as an optical system 603, for transmitting and focusing the source radiation to a sample 604; a means, such as an optical system 606, for collecting the emitted radiation; a means, such as a sub-wavelength resonant grating filter 608, for removing from the emitted radiation a desired wavelength; a means, such as a processor 610, for dispersing or separating the emitted radiation into component wavelengths; and a means, such as a detector 612, for detecting the radiation. A means, such as a computer 614, can be provided for controlling the radiation source, data acquisition and/or providing sample identification information, and so forth. The sub-wavelength resonant grating filter 608 can include a means, such as a filter mount 616, for controlling the orientation of the resonant grating filter with respect to an incident beam. The Raman system can comprise a surface-enhanced Raman system.

An exemplary radiation source 602 is a laser, which can emit high intensity, monochromatic radiation. Lasers that can be used to generate Raman scattering from a sample include gas lasers such as helium-neon, nitrogen, argon ion and krypton ion lasers; solid state lasers such as ruby lasers or neodymium-yttrium-aluminum-garnet (Nd-YAG) lasers; dye lasers; and diode lasers, such as single-mode and multi-mode diode lasers. The intensity of the output from a laser can be increased by reflecting the laser beam through a multi-pass cell or a cavity with gain media. Exemplary optical systems 603, 606 include lenses, mirrors, prisms and other optics (e.g., optical fibers).

The processor 610 can be a spectrometer, which can separate the scattered radiation into its component wavelengths, and which can comprise a Fourier transform spectrometer or other spectrometer suitable for focusing and collimating the scattered radiation. A reference laser (not shown) can be provided for optically aligning the radiation source and/or transmitting/focusing means with the resonant grating filter, spectrometer and/or photodetector.

The photodetector 612 can comprise a photodiode array (PDA) or a charge coupled device (CCD). Array photodetectors comprise multiple optical elements that can simultaneously observe a region of the scattered spectrum. Also disclosed is a photodiode with integrated sub-wavelength resonant grating filter.

Figure 7:
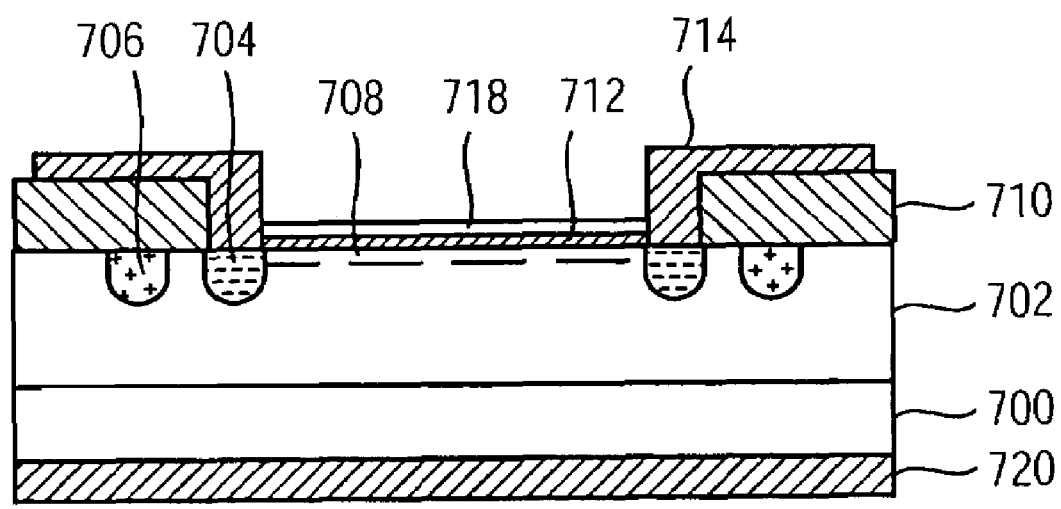
FIG. 7 is a schematic illustration of a single photodiode comprising a sub-wavelength resonant grating filter.

FIG. 7 illustrates a cross-section of an exemplary photodiode with an integrated resonant grating filter. The photodiode can be fabricated using VLSI (Very Large Scale Integration) or ULSI (Ultra Large Scale Integration) processes. A substrate 700 comprises a doped semiconductor material (e.g., silicon or gallium arsenide). The substrate 700 can be doped p-type or n-type, though the exemplary photodiode will be described herein with reference to a p-type substrate. A p-type epitaxial layer 702, which can have a thickness of from about 1 to 100 microns, is formed over the substrate 700. An n+ electrical contact region 704, a p+ channel stop region 706, and a doped (e.g., phosphorous-doped or arsenic-doped) defect-free n-type region 708 are formed in the epitaxial layer, and a field oxide layer 710 is formed over the epitaxial layer. A passivating oxide layer 712 is formed over the epitaxial layer, and an electrically conductive (e.g., aluminum) layer 714 is formed over the electrical contact region 704 and over the field oxide layer 710. The thickness of the passivating oxide layer 712 can be from about 50 nm to about 500 nm. The electrically conductive layer 714 can be used to form electrical contacts (e.g., via wire bonds, not shown). A sub-wavelength resonant grating filter 718 is formed over the passivating oxide layer 712 (i.e., over the photodiode active surface). An electrically-conductive (e.g., gold-chromium) electrical contact layer 720 can be formed on the backside of the photodiode.

An integrated photodiode-filter comprises a substrate (such as a semiconductor, plastic, glass or other suitable substrate), at least one photodiode comprising an active surface formed in and on the semiconductor substrate; and an integrated sub-wavelength resonant grating filter, wherein the sub-wavelength resonant grating filter comprises a waveguide layer formed on the active surface and a patterned layer comprising an array of diffraction elements formed on the waveguide layer. The resonant grating filter can be configured to cover a single photodiode or any one or more photodiodes of a photodiode array.

An exemplary method for measuring the chemical composition of a sample using Raman spectroscopy comprises irradiating the chemical composition with a substantially monochromatic radiation source, directing radiation scattered and/or emitted from the chemical composition through a sub-wavelength resonant grating filter, the sub-wavelength resonant grating filter comprising a diffraction structure having a characteristic period and a characteristic height, and a waveguide layer, and detecting radiation transmitted through the filter.

The period of the diffraction structure and/or the height of the diffraction structure can be determined as a function of the radiation source and/or the one or more chemical constituents in order to minimize the intensity of the elastically-scattered radiation transmitted through the filter.

The radiation source can be tuned to match the absorption band of the resonant grating filter or, more preferably, the resonant grating filter can be tuned to match the output wavelength of the radiation source. For example, the resonant wavelength of the resonant grating filter can be changed by changing the orientation of the filter with respect to a beam incident upon the filter.

At normal incidence ($\Phi=90°$) the filter can be used reject a resonant wavelength, $\lambda°_{res}$. However, by aligning (e.g., tilting) the filter with respect to the incident beam such that the angle between the incident beam and the plane of the filter is less than 90°, the filter can display a symmetric shift in the resonant response. For tilt angles up to about 5°, the filter can reject incident radiation at two wavelengths. The resonant wavelengths of the two reflected peaks for non-normal incidence can be expressed as $\lambda_{res}=\lambda°_{res}\pm\lambda$, where $\lambda$ is a change in the resonant wavelength. In an exemplary embodiment, by tilting the resonant grating filter by up to about 5°, the value of the resonant wavelength can be increased (and decreased) by up to about 40 nm. At deviations from the normal of greater than about 5°, the resonant filter characteristics typically break down. Thus, an exemplary Raman system comprises a sub-wavelength resonant grating filter and control means for adjusting the orientation (i.e., tilt angle) of the filter with respect to a beam of radiation incident upon the filter.

A Raman system comprising a sub-wavelength resonant grating filter may further be refined by incorporating a feedback control system for directing an emitted or scattered beam through the resonant grating filter, a photodetector positioned to intercept the radiation after is passes through the filter, and means for controlling the orientation of the resonant grating filter with respect to the emitted or scattered beam. By tuning the rejection wavelength of the resonant grating filter to the operating wavelength of the radiation source, the intensity of the operating wavelength that will reach the photodetector can be reduced.

Means for controlling the tilt angle of the resonant grating filter can comprise a filter mount and can be coupled to the photodetector through feedback circuitry. Available feedback methods can be used to control the tilt angle of the resonant grating filter in order to minimize the intensity of radiation impinging the photodetector at a given wavelength.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. A Raman system comprising:
   a radiation source;
   a detector positioned to receive radiation from the radiation source; and
   a sub-wavelength resonant grating filter positioned between the radiation source and the detector, wherein the sub-wavelength resonant grating filter comprises a waveguide layer and a patterned layer comprising an array of diffraction elements
   wherein the diffraction elements have an aspect ratio of between about 0.1 and 2, the aspect ratio being a ratio of height of one of the diffraction elements to a lateral dimension of the diffraction element;
   wherein the Raman system comprises a surface-enhanced Ramen system.

2. The system of claim 1, wherein the patterned layer is a single patterned layer.

3. The system of claim 1, wherein the diffraction elements are circular pillars projecting above the waveguide layer.

4. The system of claim 1, wherein the diffraction elements are recessed holes projecting into the waveguide layer.

5. The system of claim 1, wherein the diffraction elements have a lateral dimension of less than about 500 nm.

6. The system of claim 1, wherein the diffraction elements have a height above the waveguide layer of less than about 500 nm.

7. The system of claim 1, wherein the diffraction elements have a height above the waveguide layer of about 50 nm.

8. The system of claim 1, wherein the patterned layer comprises a two-dimensional array having a periodicity in first and second orthogonal directions.

9. The system of claim 8, wherein the periodicities in the first and second orthogonal directions are equal.

10. The system of claim 1, wherein the spacing between successive diffraction elements is less than about 500 nm.

11. The system of claim 1, wherein the waveguide layer is a substantially planar waveguide layer.

12. The system of claim 1, wherein the waveguide layer has a thickness of less than about 500 nm.

13. The system of claim 1, wherein the index of refraction of the waveguide layer is greater than the effective index of refraction of the patterned layer.

14. The system of claim 1, wherein the height of the diffraction elements is less than the thickness of the waveguide layer.

15. The system of claim 1, comprising a substrate layer wherein the waveguide layer is formed over the substrate layer.

16. The system of claim 15, wherein the substrate comprises a fused silica substrate having a thickness of greater than about 0.5 mm.

17. The system of claim 15, wherein the substrate comprises a photodetector array or an optical lens.

18. The system of claim 15, wherein the index of refraction of the waveguide layer is greater than the index of refraction of the substrate layer.

19. The system of claim 1, wherein the patterned layer and the waveguide layer are formed from an optically transparent dielectric material selected from the group consisting of silicon oxide, silicon nitride, silicon oxynitride, hafnium oxide and tantalum oxide, and mixtures thereof.

20. The system of claim 1, wherein the patterned layer and the waveguide layer are formed from the same material.

21. The system of claim 1, wherein the resonant grating filter is adapted to have an extinction ratio for a characteristic wavelength of radiation of at least 10.

22. A Raman system comprising:
a radiation source;
a detector positioned to receive radiation from the radiation source; and
a sub-wavelength resonant grating filter positioned between the radiation source and the detector, wherein the sub-wavelength resonant grating filter comprises a waveguide layer and a patterned layer comprising an array of diffraction elements;
wherein the resonant grating filter is adapted to reduce the intensity of elastically scattered radiation by at least 90%.

23. The system of claim 1, wherein at least one of the patterned layer and the waveguide layer comprise an antireflective coating.

24. The system of claim 1, wherein the sub-wavelength resonant grating filter is mounted on a filter mount.

25. A Raman system comprising:
means for irradiating a sample with excitation radiation of a single wavelength;
means for detecting scattered radiation from the sample irradiated with the excitation radiation; and
a sub-wavelength resonant grating filter for removing from the scattered radiation a characteristic wavelength of radiation prior to detecting the scattered radiation, wherein the sub-wavelength resonant grating filter comprises a waveguide layer and a patterned layer comprising an array of diffraction elements;
wherein the diffraction elements have an aspect ratio of between about 0.1 and 2, the aspect ratio being a ratio of height of one of the diffraction elements to a lateral dimension of the diffraction element;
wherein the Raman system comprises a surface-enhanced Raman system.

26. A method for measuring by Raman spectroscopy one or more selected constituents of a chemical composition, comprising:
irradiating with a substantially monochromatic radiation source a chemical composition comprising the one or more chemical constituents;
directing radiation scattered and/or emitted from the chemical composition through a sub-wavelength resonant grating filter, the sub-wavelength resonant grating filter comprising a waveguide layer and an array of diffraction elements having a characteristic period and a characteristic height, and
detecting radiation transmitted through the filter;
wherein the diffraction elements have an aspect ratio of between about 0.1 and 2, the aspect ratio being a ratio of height of one of the diffraction elements to a lateral dimension of the diffraction element;
wherein the Raman system comprises a surface-enhanced Raman system.

27. The method of claim 26, comprising selecting the period of the diffraction elements and/or the height of the diffraction elements as a function of the radiation source and/or the one or more constituents in order to minimize the intensity of the elastically-scattered radiation transmitted through the filter.

28. The method of claim 26, comprising selecting the orientation of the sub-wavelength resonant grating filter with respect to the scattered and/or emitted radiation incident upon the filter in order to minimize the intensity of the elastically-scattered radiation transmitted through the filter.

29. An integrated photodiode-filter comprising:
a substrate, at least one photodiode comprising an active surface formed in and on the substrate; and
an integrated sub-wavelength resonant grating filter, wherein the sub-wavelength resonant grating filter comprises a waveguide layer formed on the active surface and a patterned layer comprising an array of diffraction elements formed on the waveguide layer.

30. The integrated photodiode-filter of claim 29, wherein the patterned layer is a single patterned layer.

31. The integrated photodiode-filter of claim 29, wherein the diffraction elements are circular pillars projecting above the waveguide layer.

32. The integrated photodiode-filter of claim 29, wherein the diffraction elements have a lateral dimension of less than about 500 nm.

33. The integrated photodiode-filter of claim 29, wherein the diffraction elements have a height above the waveguide layer of less than about 500 nm.

34. The integrated photodiode-filter of claim 29, wherein the patterned layer comprises a two-dimensional array having a periodicity in first and second orthogonal directions.

35. The integrated photodiode-filter of claim 34, wherein the periodicities in the first and second orthogonal directions are equal.

36. The integrated photodiode-filter of claim 29, wherein the spacing between successive diffraction elements is less than about 500 nm.

37. The integrated photodiode-filter of claim 29, wherein the waveguide layer is a substantially planar waveguide layer.

38. The integrated photodiode-filter of claim 29, wherein the index of refraction of the waveguide layer is greater than the effective index of refraction of the patterned layer.

39. The integrated photodiode-filter of claim 29, wherein the patterned layer and the waveguide layer are formed from an optically transparent dielectric material selected from the group consisting of silicon oxide, silicon nitride, silicon oxynitride, hafnium oxide and tantalum oxide, and mixtures thereof.

* * * * *

UNITED STATES PATENT AND TRADEMARK OFFICE
CERTIFICATE OF CORRECTION

PATENT NO. : 7,474,396 B2  
APPLICATION NO. : 11/257073  
DATED : January 6, 2009  
INVENTOR(S) : Wei Wu et al.

Page 1 of 1

It is certified that error appears in the above-identified patent and that said Letters Patent is hereby corrected as shown below:

In column 8, line 59, in Claim 1, delete "Ramen" and insert -- Raman --, therefor.

Signed and Sealed this

Twenty-first Day of July, 2009

JOHN DOLL  
*Acting Director of the United States Patent and Trademark Office*